US006846333B2

(12) United States Patent
Legrand et al.

(10) Patent No.: US 6,846,333 B2
(45) Date of Patent: Jan. 25, 2005

(54) KERATIN FIBER DYEING COMPOSITION COMPRISING A PARTICULAR AMINOSILICONE

(75) Inventors: Frédéric Legrand, Courbevoie (FR); Jean-Marie Millequant, Saint-Maur des Fosses (FR)

(73) Assignee: L'Oreal, S.A. (FR)

(*) Notice: Subject to any disclaimer, the term of this patent is extended or adjusted under 35 U.S.C. 154(b) by 104 days.

(21) Appl. No.: 10/290,368

(22) Filed: Nov. 8, 2002

(65) Prior Publication Data

US 2003/0140429 A1 Jul. 31, 2003

(30) Foreign Application Priority Data

Nov. 8, 2001 (FR) .......................................... 01 14467

(51) Int. Cl.$^7$ ................................................. A61K 7/13
(52) U.S. Cl. ...................... 8/405; 8/406; 8/410; 8/421; 8/552; 8/581; 8/632; 424/70.1; 424/70.2; 424/70.11
(58) Field of Search ............................ 8/405, 406, 410, 8/421, 552, 581, 632; 424/70.1, 70.2, 70.11

(56) References Cited

U.S. PATENT DOCUMENTS

| | | | |
|---|---|---|---|
| 2,261,002 A | 10/1941 | Ritter ......................... | 260/570 |
| 2,271,378 A | 1/1942 | Searle ......................... | 167/22 |
| 2,273,780 A | 2/1942 | Dittmar ....................... | 260/28 |
| 2,375,853 A | 5/1945 | Kirby et al. ................. | 288/588 |
| 2,388,614 A | 11/1945 | Kirby et al. ................. | 167/22 |
| 2,454,547 A | 11/1948 | Bock et al. ................. | 260/567.6 |
| 2,528,378 A | 10/1950 | Mannheimer ............. | 260/209.4 |
| 2,781,354 A | 2/1957 | Mannheimer ............. | 260/349.6 |
| 2,961,347 A | 11/1960 | Floyd ........................ | 117/141 |
| 3,206,462 A | 9/1965 | McCarty ................... | 260/256.4 |
| 3,227,615 A | 1/1966 | Korden ...................... | 167/87.1 |
| 3,589,578 A | 6/1971 | Kamphausen .............. | 226/40 |
| 3,632,559 A | 1/1972 | Matter et al. ............... | 260/78 |
| 3,874,870 A | 4/1975 | Green et al. ................ | 71/67 |
| 3,917,817 A | 11/1975 | Vanlerberghe et al. ...... | 424/70 |
| 3,929,990 A | 12/1975 | Green et al. ................ | 424/78 |

(List continued on next page.)

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| DE | 197 54 053 | 6/1999 |
| EP | 0 122 324 | 10/1984 |
| EP | 0 714 954 | 6/1996 |
| EP | 0 890 355 | 1/1999 |
| FR | 1 400 366 | 5/1963 |
| FR | 1 492 597 | 9/1966 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 733 749 | 11/1996 |
| GB | 1 026 978 | 4/1966 |
| GB | 1 153 196 | 5/1969 |
| GB | 2 165 550 | 4/1986 |
| JP | 88 169571 | 7/1988 |
| JP | 91 10659 | 1/1991 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |

OTHER PUBLICATIONS

English language Derwent Abstract of DE 197 54 053, Jun. 10, 1999.
English language Derwent Abstract of FR 1 400 366, May 15, 1963.
English language Derwent Abstract of FR 1 492 597, Sep. 13, 1966.
English language Derwent Abstract of FR 2 077 143, Oct. 15, 1971.
English language Derwent Abstract of FR 2 080 759, Nov. 19, 1971.
English language Derwent Abstract of FR 2 320 330, Mar. 4, 1977.
English language Derwent Abstract of FR 2 336 434, Jul. 22, 1977.
English language Derwent Abstract of JP 88 169571, Jul. 13, 1988.
English language Derwent Abstract of JP 91 10659, Jan. 18, 1991.
M.R. Porter. BSc, PhD, CChem, MRSC, "Handbook of Surfactants," Blackie & Son Ltd., 1991, pp. 116–178.

*Primary Examiner*—Yogendra N. Gupta
*Assistant Examiner*—Eisa Elhilo
(74) *Attorney, Agent, or Firm*—Finnegan, Henderson, Farabow, Garrett & Dunner LLP

(57) ABSTRACT

The disclosure relates to a composition for dyeing human keratin fibres, such as hair, comprising in a cosmetically acceptable medium at least one direct dye or at least one oxidation dye and at least one aminosilicone.

The disclosure further relates to dyeing devices and methods employing the composition.

74 Claims, No Drawings

U.S. PATENT DOCUMENTS

| | | | |
|---|---|---|---|
| 3,966,904 A | 6/1976 | Green et al. | 424/78 |
| 4,001,432 A | 1/1977 | Green et al. | 424/329 |
| 4,003,699 A | 1/1977 | Rose et al. | 8/10.2 |
| 4,005,193 A | 1/1977 | Green et al. | 424/168 |
| 4,013,787 A | 3/1977 | Varlerberghe et al. | 424/70 |
| 4,025,617 A | 5/1977 | Green et al. | 424/78 |
| 4,025,627 A | 5/1977 | Green et al. | 424/248 |
| 4,025,653 A | 5/1977 | Green et al. | 424/325 |
| 4,026,945 A | 5/1977 | Green et al. | 260/567 |
| 4,027,008 A | 5/1977 | Sokol | 424/62 |
| 4,027,020 A | 5/1977 | Green et al. | 424/248.56 |
| 4,031,307 A | 6/1977 | DeMartino et al. | 536/114 |
| 4,131,576 A | 12/1978 | Iovine et al. | 260/17.4 |
| 4,157,388 A | 6/1979 | Christiansen | 424/70 |
| 4,172,887 A | 10/1979 | Vanlerberghe et al. | 424/70 |
| 4,223,009 A | 9/1980 | Chakrabarti | 424/47 |
| 4,277,581 A | 7/1981 | Vanlerberghe et al. | 525/420 |
| 4,349,532 A | 9/1982 | Vanlerberghe et al. | 424/47 |
| 4,591,610 A | 5/1986 | Grollier | 524/55 |
| 4,608,250 A | 8/1986 | Jacquet et al. | 424/71 |
| 4,702,906 A | 10/1987 | Jacquet et al. | 424/70 |
| 4,710,314 A * | 12/1987 | Madrange et al. | 510/122 |
| 4,719,282 A | 1/1988 | Nadolsky et al. | 528/310 |
| 4,761,273 A | 8/1988 | Grollier et al. | 424/47 |
| 4,839,166 A | 6/1989 | Grollier et al. | 424/71 |
| 5,009,880 A | 4/1991 | Grollier et al. | 424/47 |
| 5,061,289 A | 10/1991 | Clausen et al. | 8/405 |
| 5,139,037 A | 8/1992 | Grollier et al. | 132/203 |
| 5,196,189 A | 3/1993 | Jacquet et al. | 424/72 |
| 5,380,340 A | 1/1995 | Neunhoeffer et al. | 8/409 |
| 5,534,267 A | 7/1996 | Neunhoeffer et al. | 29/840 |
| 5,663,366 A | 9/1997 | Neunhoeffer et al. | 548/371.4 |
| 5,708,151 A | 1/1998 | Möckli | 534/608 |
| 5,766,576 A | 6/1998 | Lowe et al. | 424/62 |
| 5,958,392 A | 9/1999 | Grollier et al. | 424/70.17 |
| 5,989,295 A * | 11/1999 | de la Mettrie et al. | 8/406 |
| 6,284,003 B1 | 9/2001 | Rose et al. | 8/412 |
| 6,645,258 B2 | 11/2003 | Vidal et al. | 8/405 |

\* cited by examiner

KERATIN FIBER DYEING COMPOSITION COMPRISING A PARTICULAR AMINOSILICONE

The present disclosure relates to a composition for dyeing human keratin fibres, such as hair, comprising at least one direct dye or oxidation dye and at least one aminosilicone.

In principle, there are two methods of dyeing human keratin fibres, such as hair: direct dyeing and oxidation dyeing. Direct dyeing employs direct dyes and/or pigments that are coloured molecules. These direct dyes and/or pigments give the fibres a temporary colour, which fades after several shampooings. Direct dyeing may be carried out in the presence or absence of oxidizing agents. Oxidation dyeing employs oxidation dye precursors and an oxidizing agent, and imparts to the fibres a colour that is longer-lasting than direct dyeing. The use of an oxidizing agent may involve a certain degree of degradation of the keratin fibre.

An increase in the frequency of shampooing may lead to greater degradation of a keratin fibre dyeing between applications.

Consequently, there exists a need to improve the durability of the direct dyeing or oxidation dyeing, especially with respect to shampooing.

After considerable research, the inventors have discovered, quite unexpectedly and surprisingly, that the use of a composition comprising at least one direct dye or at least one oxidation dye and at least one aminosilicone allows at least one problem described above to be solved.

The composition allows the condition of the fibre to be improved. Improving the condition of the fibre may mean, for example, reducing the porosity or the alkaline solubility of the fibre and improving cosmetic properties, such as smoothness, softness and ease of disentangling and styling.

This effect is remanent, e.g., durable.

The porosity is measured, for example, by the binding of 2-nitro-para-phenylenediamine at 0.25% in an ethanol/pH 10 buffer mixture (volume ratio 10/90) at 37° C. and a pH of 10 in 2 minutes.

The alkaline solubility corresponds, for example, to the loss in mass of a sample of 100 mg of keratin fibres under the action of decinormal sodium hydroxide solution at 65° C. for 30 minutes.

This discovery partially forms the basis of the present disclosure.

An embodiment provides a composition for dyeing human keratin fibres, such as hair, comprising in a cosmetically acceptable medium at least one direct dye or at least one oxidation dye, and further comprising at least one aminosilicone chosen from formulae (I) and (II), these formulae being described below.

Another embodiment provides a ready-to-use composition for dyeing human keratin fibres comprising at least one direct dye or at least one oxidation dye and at least one aminosilicone chosen from formulae (I) and (II), these formulae being described below, and at least one oxidizing agent.

A "ready-to-use composition" means a composition intended for application as it is to the keratin fibres, e.g., it may be stored before use or may result from the extemporaneous mixing of at least two compositions.

Another embodiment provides a method of dyeing human keratin fibres, such as hair, comprising applying to the fibres at least one colouring composition comprising, in a cosmetically acceptable medium, at least one direct dye and at least one aminosilicone chosen from formulae (I) and (II).

Another embodiment provides a method of dyeing human keratin fibres, such as hair, comprising applying to the fibres at least one colouring composition comprising, in a cosmetically acceptable medium, at least one direct dye or at least one oxidation dye and at least one aminosilicone chosen from formulae (I) and (II). The colour may be developed at alkaline, neutral or acidic pH by means of at least one oxidizing composition comprising at least one oxidizing agent. The at least one oxidizing composition may be mixed at the time of use with the at least one colouring composition, or the at least one colouring composition and the at least one oxidizing composition may be applied sequentially without rinsing in between applications.

A further embodiment provides for multi-compartment a dyeing device or kit.

In an embodiment, a multi-compartment kit may comprise a first compartment comprising a composition comprising, in a cosmetically acceptable medium, at least one direct dye or at least one oxidation dye and at least one aminosilicone chosen from formulae (I) and (II). A multi-compartment kit may comprise a second compartment comprising a composition comprising, in a cosmetically acceptable medium, at least one oxidizing agent.

In another embodiment, a multi-compartment device may comprise a first compartment comprising a composition comprising, in a cosmetically acceptable medium, at least one direct dye or at least one oxidation dye, a second compartment comprising a composition comprising, in a cosmetically acceptable medium, at least one oxidizing agent, and a third compartment comprising a composition comprising, in a cosmetically acceptable medium, at least one aminosilicone chosen from formulae (I) and (II).

At least one other characteristic, aspect, subject matter and advantage of the invention will appear more clearly to a person of ordinary skill in the art upon reading the description and examples which follow.

Aminosilicone

The at least one aminosilicone chosen from formula (I) and (II) comprises:

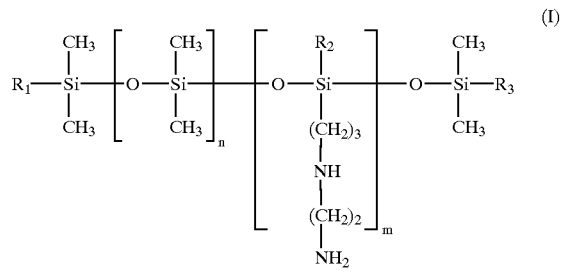

wherein:

m and n are numbers with a sum (n+m) ranging, for example, from 1 to 1000 and further, for example, from 50 to 250 and still further, for example, from 100 to 200;

n is a number ranging from 0 to 999 and, for example, from 49 to 249 and further, for example, from 125 to 175, and m is a number ranging from 1 to 1000 and, for example, from 1 to 10, and further, for example, from 1 to 5;

$R_1$, $R_2$ and $R_3$, which may be identical or different, are chosen from a hydroxyl radical and $C_1$–$C_4$ alkoxy radicals, at least one of the radicals $R_1$ to $R_3$ chosen from alkoxy radicals.

The alkoxy radical may be, for example, a methoxy radical.

The hydroxy/alkoxy molar ratio may, for example, range from 0.2:1 to 0.4:1 and, for example, from 0.25:1 to 0.35:1 and further, for example, may be equal to 0.3.

The at least one aminosilicone of formula (I) may have a weight-average molecular mass ranging, for example, from 2000 to 1 000 000, for example from 3500 to 200 000.

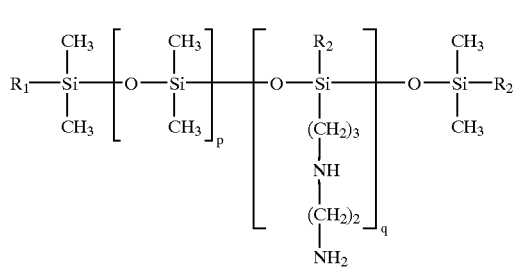

wherein:

p and q are numbers with a sum (p+q), for example, ranging from 1 to 1000, for example from 50 to 350 and further, for example, from 150 to 250; p is a number ranging from 0 to 999, for example from 49 to 349, and further, for example, from 159 to 239, and q is a number ranging from 1 to 1000, for example, from 1 to 10, and further, for example, from 1 to 5;

$R_1$ and $R_2$, which are different, are chosen from a hydroxyl radical and $C_1$–$C_4$ alkoxy radicals, at least one of the radicals $R_1$ and $R_2$ being chosen from alkoxy radicals.

The alkoxy radical may be, for example, a methoxy radical.

The hydroxy/alkoxy molar ratio may, for example, range from 1:0.8 to 1:1.1, for example from 1:0.9 to 1:1, and may further, for example, be 1:0.95.

The at least one aminosilicone of formula (II) may have a weight-average molecular mass ranging, for example, from 2000 to 200 000, for example from 5000 to 100 000, and further, for example, from 10 000 to 50 000.

The weight-average molecular mass of the at least one aminosilicone are measured by gel permeation chromatography (GPC) at ambient temperature in polystyrene equivalents. The columns used are $\mu$ Styragel columns. The eluent is THF and the flow rate is 1 ml/min. 200 $\mu$l of a 0.5% by weight solution of silicone in THF are injected. Detection is carried out by refractometry and UV metry.

An embodiment comprising the at least one aminosilicone chosen from formulae (I) and (II) may further comprise at least one aminosilicone whose formula may be different from the at least one aminosilicone chosen from formulae (I) and (II).

A product comprising the at least one aminosilicone of structure (I) is provided, for example, by the company Wacker under the name Belsil ADM 652®.

Products comprising the at least one aminosilicone of structure (II) are provided, for example, by the company Wacker under the name Fluid WR 1300® and Belsil ADM 6057®.

The at least one aminosilicone chosen from formulae (I) and (II) may be employed, for example, in an oil-in-water emulsion. The oil-in-water emulsion may further comprise at least one surfactant. The at least one surfactant may be chosen, for example, from cationic and non-ionic surfactants.

A particle of the at least one aminosilicone in the emulsion may have an average size ranging, for example, from 3 to 500 nanometres. Such particle sizes are measured with a laser granulometer.

The at least one aminosilicone of formula (II) may be used, for example, in an microemulsion. In the microemulsion, the at least one aminosilicone of formula (I) may have a size ranging from 5 to 60 nanometres and, for example, from 10 to 50 nanometres.

A microemulsion of the at least one aminosilicone of formula (II) may be available, for example, under the name Finish CT 96 E® or SLM 28020® by the company Wacker.

The at least one aminosilicone chosen from formulae (I) and (II) may be selected, for example, such that the contact angle with water of a hair treated with a composition comprising 2% AS (active substance) of the at least one aminosilicone ranges from 90 to 180°, for example from 90 to 130°.

A composition comprising the at least one aminosilicone chosen from formulae (I) and (II) may be such that the contact angle of a hair treated with the composition ranges from 90 to 180°, for example from 90 to 130°.

The measurement of the contact angle is based, for example, on the immersion of a hair in distilled water. The measurement consists of evaluating the force exerted by the water on the hair during its immersion in the distilled water and during its withdrawal. The forces measured are directly related to the contact angle θ between the water and the surface of the hair. The hair is hydrophilic when the angle θ ranges from 0 to less than 90° and hydrophobic when this angle ranges from 90 to 180°.

The test is carried out using locks of natural hair which have been bleached under identical conditions and then washed.

Each lock of 1 gram is placed in a 75 mm-diameter crystallizer and then covered homogeneously with 5 ml of the formula under test. The lock is left in this condition for 15 minutes at ambient temperature and then rinsed for 30 seconds. After being wrung out, the lock is left in the open air until completely dry.

For example, 10 hairs having undergone the same treatment are analysed. Each sample, fixed to a precision microbalance, is immersed by the end into a container filled with distilled water. This balance, which is a DCA (dynamic contact angle analyser) from the company CAHN Instruments, allows measurement of the force (F) exerted by the water on the hair.

The perimeter (P) of the hair is measured via microscopic observation. The average wettability force over 10 hairs and the cross section of the hairs analysed allow the contact angle of the hair with water to be obtained, in accordance with the following formula:

$$F = P * \Gamma lv * \cos\theta$$

where F is the wettability force expressed in newtons, P is the perimeter of the hair, in metres, Γlv is the liquid/water vapour interfacial tension, in $J/m^2$, and θ is the contact angle.

For example, the product SLM 28020® from Wacker at 12% in water (i.e. 2% of at least one aminosilicone) gives a contact angle of 93° in the test indicated above.

The at least one aminosilicone chosen from formulae (I) and (II) may be used, for example, in a dyeing composition in an amount ranging from 0.01 to 20% by weight of the total weight of the composition. For example, this amount may range from 0.1 to 15% by weight, for example from 0.5 to 10% by weight.

Oxidation Dyes

In one embodiment, at least one oxidation dye may be used, and the at least one oxidation dye may be chosen from oxidation bases and couplers.

In another embodiment, the composition may comprise, for example, at least one oxidation base.

The at least one oxidation base may be chosen from oxidation bases conventionally known in the art of oxidation dyeing, which include, for example, ortho- and para-phenylenediamines, double bases, ortho- and para-aminophenols, the heterocyclic bases below, and their acid addition salts.

The at least one oxidation base may be chosen, for example, from the following:

(A) at least one para-phenylenediamine of formula (III) and its acid addition salts:

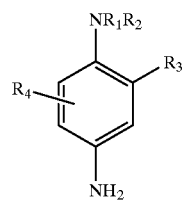

wherein:

$R_1$ is chosen from a hydrogen atom and $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, $C_1$–$C_4$ alkyl radicals substituted by at least one nitrogenous group, phenyl radicals, and 4-aminophenyl radicals;

$R_2$ is chosen from a hydrogen atom and $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, and $C_1$–$C_4$ alkyl radicals substituted by at least one nitrogenous group;

$R_1$ and $R_2$ may also form, with the nitrogen atom to which they are attached, a 5- or 6-membered nitrogenous heterocycle optionally substituted by at least one group chosen from alkyl groups, hydroxyl groups and ureido groups;

$R_3$ is chosen from a hydrogen atom, halogen atoms, such as a chlorine atom, and $C_1$–$C_4$ alkyl radicals, sulpho radicals, carboxyl radicals, $C_1$–$C_4$ monohydroxyalkyl radicals, $C_1$–$C_4$ hydroxyalkoxy radicals, $C_1$–$C_4$ acetylaminoalkoxy radicals, $C_1$–$C_4$ mesylaminoalkoxy radicals, and $C_1$–$C_4$ carbamoylaminoalkoxy radicals; and $R_4$ is chosen from a hydrogen and halogen atoms and $C_1$–$C_4$ alkyl radicals.

At least one nitrogenous group of the formula (III) above may be chosen from, for example, amino radicals, mono($C_1$–$C_4$)alkylamino radicals, di($C_1$–$C_4$)alkylamino radicals, tri($C_1$–$C_4$)alkylamino radicals, monohydroxy($C_1$–$C_4$) alkylamino radicals, imidazolinium radicals, and ammonium radicals.

At least one para-phenylenediamine of formula (III) above may be chosen, for example, from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, and their acid addition salts.

At least one para-phenylenediamine of formula (III) above may be chosen, for example, from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and their acid addition salts.

(B) At least one double base may be chosen from compounds comprising at least two aromatic nuclei which carry at least one group chosen from amino groups and hydroxyl groups.

The at least one double base which may be used as at least one oxidation base may be chosen from, for example, compounds of formula (IV) below and their acid addition salts:

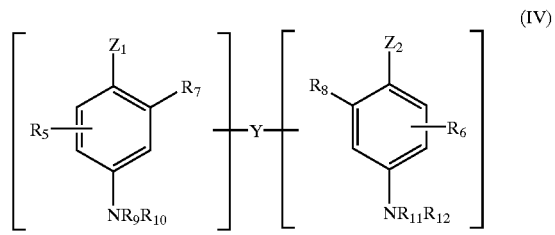

wherein:

$Z_1$ and $Z_2$, which may be identical or different, are chosen from a hydroxyl group and —$NH_2$ radicals which may be substituted by $C_1$–$C_4$ alkyl radicals or by a linking arm Y; the linking arm Y is chosen from alkylene chains comprising from 1 to 14 carbon atoms, which may be linear or branched, and may be interrupted and/or terminated by at least one nitrogenous group and/or by at least one heteroatom, such as an oxygen, sulphur or nitrogen atom, and may be optionally substituted by at least one group chosen from a hydroxyl group and $C_1$–$C_6$ alkoxy radicals;

$R_5$ and $R_6$, which may be identical or different, are chosen from a hydrogen atom and halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, and a linking arm Y;

$R_7$, $R_8$, $R_9$, $R_{10}$, $R_{11}$ and $R_{12}$, which may be identical or different, are chosen from a hydrogen atom, a linking arm Y, and $C_1$–$C_4$ alkyl radicals;

subject to the proviso that the a compounds of formula (IV) comprises only one linking arm Y per molecule.

At least one nitrogenous group of the formula (IV), for example, may be chosen from amino groups, mono($C_1$–$C_4$) alkylamino groups, di($C_1$–$C_4$)alkylamino groups, tri($C_1$–$C_4$) alkylamino groups, monohydroxy($C_1$–$C_4$)alkylamino groups, imidazolinium groups, and ammonium radical groups.

At least one double base of formula (IV) above may be chosen, for example, from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenol)tetramethylene-diamie, N,N'-bis(ethyl)-N,N'-bis(4'-amino-3'-methylphenyl) ethylenediamine, 1,8-bis(2,5-diaminophenoxy)-3,5-dioxaoctane, and their acid addition salts.

At least one double base of formula (IV) further may comprise, for example, N,N'-bis(β-hydroxyethyl)-N,N'-bis (4'-aminophenyl)-1,3-diaminopropanol, 1,8-bis(2,5-diaminophenoxy)-3,5-dioxaoctane or one of their acid addition salts.

(C) At least one para-aminophenol may be chosen, for example, from compounds of the formula (V) below and their acid addition salts:

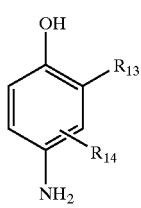

(V)

wherein:

$R_{13}$ is chosen from a hydrogen atom, halogen atoms, such as fluorine, and $C_1$–$C_4$ alkyl radicals, $C_1$–$C_4$ monohydroxyalkyl radicals, ($C_1$–$C_4$)alkoxy($C_1$–$C_4$)alkyl radicals, $C_1$–$C_4$ aminoalkyl radicals, and $C_1$–$C_4$ hydroxy($C_1$–$C_4$) alkylaminoalkyl radicals; and $R_{14}$ is chosen from a hydrogen atom, halogen atoms such as fluorine, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, $C_1$–$C_4$ cyanoalkyl radicals, and ($C_1$–$C_4$) alkoxy($C_1$–$C_4$)alkyl radicals.

At least one para-aminophenol of formula (V) may be chosen from, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their acid addition salts.

(D) At least one ortho-aminophenol, which may be used as the at least one oxidation base, may be chosen from, for example, 2-aminophenol, 2-amino-1-hydroxy-5-methylbenzene, 2-amino-1-hydroxy-6-methylbenzene, 5-acetamido-2-aminophenol, and their acid addition salts.

(E) At least one heterocyclic base, which may comprise the at least one oxidation base, may be chosen, for example, from pyridine derivatives, pyrimidine derivatives, pyrazole derivatives, and their acid addition salts.

At least one pyridine derivative may be chosen, for example, from the compounds described in Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their acid addition salts.

At least one pyrimidine derivative may be chosen from, for example, the compounds described in German Patent No. DE 2 359 399, Japanese Patent Nos. JP 88-169 571 and JP 91-10659 and Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine and the pyrazolopyrimidine derivatives such as those mentioned in the Patent Application No. FR-A-2 750 048, and comprising pyrazolo[1,5-a] pyrimidine-3,7-diamine; 2,5-dimethylpyrazolo[1,5-a] pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo [1,5-a]pyrimidin-7-ylamino)ethanol; 2-(7-aminopyrazolo[1, 5-a]pyrimidin-3-ylamino)ethanol; 2-[(3-aminopyrazolo[1,5-a]pyrimidin-7-yl)-(2-hydroxyethyl)amino]ethanol; 2-[(7-aminopyrazolo[1,5-a]pyrimidin-3-yl)-(2-hydroxyethyl) amino]ethanol; 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine; 3-amino-5-methyl-7-imidazolylpropylamino-pyrazolo[1,5-a]pyrimidine; and their addition salts and their tautomeric forms, where a tautomeric equilibrium exists, and their acid addition salts.

At least one pyrazole derivative may be chosen from, for example, the compounds described in U.S. Pat. Nos. DE 3 843 892 and DE 4 133 957, and U.S. patent application Ser. Nos. WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1 -methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and their acid addition salts.

The at least one oxidation base may comprise, for example, from 0.0005 to 12% by weight of the total weight of the composition, for example, from 0.005 to 8% by weight, relative to the total weight of the composition.

At least one coupler, which may be used in another embodiment, may be chosen from couplers conventionally used in oxidation dyeing compositions, e.g., meta-aminophenols, meta-phenylenediamines, meta-diphenols, naphthols and heterocyclic couplers, such as indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines and their acid addition salts.

The at least one coupler may be chosen from, for example, 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6- dimethylpyrazolo[3,2-c]-1,2,4-triazole, 2,6-dimethylpyrazolo[1,5-b]-1,2,4-triazole and their acid addition salts.

If present, the at least one coupler may range, for example, from 0.0001 to 10% by weight of the total weight of the composition, for example from 0.005 to 5% by weight.

The at least one acid addition salt of the at least one oxidation base and/or at least one coupler is chosen, for example, from hydrochlorides, hydrobromides, sulphates, tartrates, lactates and acetates.

Direct Dyes

The at least one direct dye which may be chosen, for example, from neutral, acidic and cationic nitro benzene direct dyes, neutral, acidic and cationic azo direct dyes, neutral, acidic and cationic quinone, such as anthraquinone direct dyes, azine direct dyes, triarylmethane direct dyes, indoamine diect dyes and natural direct dyes.

At least one benzene direct dye which may be used may be chosen from, for example, the following compounds:
1,4-diamino-2-nitrobenzene
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

At least one azo direct dye which may be used may be chosen from the cationic azo dyes described in Patent Application Nos. WO 95/15144, WO 95/01772 and EP-714954.

These compounds may be chosen, for example, from the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride and
1-methyl-4-[(methylphenylhydrazono)methyl]pyridinium methyl sulphate.

The at least one azo direct dye may be chosen, for example, from the following dyes described in the Color Index International 3rd edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

The at least one azo direct dye may be further chosen from 1-(4'-aminodiphenylazo)-2-methyl-4-bis(β-hydroxyethyl)aminobenzene and 4-hydroxy-3-(2-methoxyphenylazo)-1-naphthalenesulphonic acid.

At least one quinone direct dye may be chosen, for example, from the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99
and the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

At least one azine dye may also be chosen from the following compounds:
Basic Blue 17
Basic Red 2.

At least one triarylmethane dye may be chosen, for example, from the following compounds:
Basic Green 1
Acid Blue 9
Basic Violet 3
Basic Violet 14
Basic Blue 7
Acid Violet 49
Basic Blue 26
Acid Blue 7

At least one indoamine dye may be chosen, for example, from the following compounds:
2-β-hydroxyethylamino-5-[bis-(β-4'-hydroxyethyl)amino]anilino-1,4-benzoquinone;
2-β-hydroxyethylamino-5-(2'-methoxy-4'-amino)anilino-1,4-benzoquinone;

3-N-(2'-chloro-4'-hydroxy)phenylacetylamino-6-methoxy-1,4-benzoquinoneimine;
3-N-(3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

At least one natural direct dye may be chosen, for example, from lawsone, juglone, alizarin, purpurin, carminic acid, kermesic acid, purpurogallin, protocatechaldehyde, indigo, isatin, curcumin, spinulosin and apigenidin. The at least one natural direct dye may further be chosen, for example, from extracts and decoctions comprising natural dyes, such as cataplasms or extracts based on henna.

At least one direct dye may be present in an amount ranging from, for example, 0.001 to 20% by weight of the total weight of the ready-to-use composition, for example from 0.005 to 10% by weight.

In an embodiment, a composition may further comprise at least one surfactant. The at least one surfactant may be chosen from anionic, amphoteric, nonionic, zwitterionic and cationic surfactants.

The at least one surfactant may be chosen from the following:

(i) Anionic Surfactant(s):

At least one anionic surfactant may be chosen, for example, from the following salts: alkali metal salts, sodium salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkylsulphonates, alkyl phosphates, alkylamidesulphonates, alkylarylsulphonates, α-olefinsulphonates, paraffinsulphonates; $(C_6-C_{24})$alkyl sulphosuccinates, $(C_6-C_{24})$alkyl ether sulphosuccinates, $(C_6-C_{24})$alkylamide sulphosuccinates; $(C_6-C_{24})$alkyl sulphoacetates; $(C_6-C_{24})$acyl sarcosinates and $(C_6-C_{24})$acyl glutamates. At least one anionic surfactant may further be chosen, for example, from the carboxylic esters of $(C_6-C_{24})$alkyl polyglycosides, such as alkylglucoside citrates, alkylpolyglycoside tartrates and alkylpolyglycoside sulphosuccinates, alkylsulphosuccinamates; acyl isethionates and N-acyltaurates, the alkyl radical and acyl radical of all of these various compounds, for example, comprising from 12 to 20 carbon atoms, and the aryl radical may be chosen from, for example, a phenyl group and a benzyl group. At least one anionic surfactant may also be chosen, for example, from fatty acid salts, such as the salts of oleic acid, ricinoleic acid, palmitic acid and stearic acid, coconut oil acid and hydrogenated coconut oil acid; acyl lactylates wherein the acyl radical comprises 8 to 20 carbon atoms, alkyl-D-galactosideuronic acids and their salts, polyoxyalkylenated $(C_6-C_{24})$alkyl ether carboxylic acids, polyoxyalkylenated $(C_6-C_{24})$alkyl aryl ether carboxylic acids, polyoxyalkylenated $(C_6-C_{24})$alkylamido ether carboxylic acids and their salts, such as those comprising from 2 to 50 alkylene oxide groups, such as ethylene oxide groups, and mixtures thereof.

(ii) Nonionic Surfactant(s):

At least one nonionic surfactant may be chosen, for example, from compounds that are well-known (see, for example, "Handbook of Surfactants" by M. R. Porter, published by Blackie & Son (Glasgow and London), 1991, pp. 116–178). The at least one nonionic surfactant may be chosen, for example, from polyethoxylated alkylphenols and polypropoxylated alkylphenols, alpha-diols and alcohols comprising a fatty chain comprising, for example, 8 to 18 carbon atoms, wherein the number of ethylene oxide groups and propylene oxide groups may range, for example, from 2 to 50. The at least one nonionic surfactant may also be chosen, for example, from copolymers of ethylene oxide and copolymers of propylene oxide, condensates of ethylene oxide and condensates of propylene oxide with fatty alcohols; polyethoxylated fatty amides, for example, comprising from 2 to 30 mol of ethylene oxide, polyglycerolated fatty amides comprising from 1 to 5 glycerol groups, such as from 1.5 to 4 glycerol groups; polyethoxylated fatty amines, for example, comprising from 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkyl polyglycosides, N-alkylglucamine derivatives, amine oxides such as $(C_{10}-C_{14})$alkylamine oxides and N-acylaminopropylmorpholine oxides.

(iii) Amphoteric or Zwitterionic Surfactant(s):

At least one amphoteric surfactant or at least one zwitterionic surfactant may be chosen, for example, from the following: aliphatic secondary and tertiary amine derivatives wherein the aliphatic radical comprises a linear or branched chain comprising 8 to 18 carbon atoms and comprising at least one water-solubilizing anionic group (for example, carboxylate, sulphonate, sulphate, phosphate or phosphonate); and $(C_8-C_{20})$alkylbetaines, sulphobetaines, $(C_8-C_{20})$alkylamido$(C_1-C_6)$alkylbetaines and $(C_8-C_{20})$alkylamido$(C_1-C_6)$alkylsulphobetaines.

At least one amine derivative may be sold under the name Miranol, as described in U.S. Pat. Nos. 2,528,378 and 2,781,354, and classified in the CTFA dictionary, 3rd edition, 1982, under the names amphocarboxyglycinates and amphocarboxypropionates of respective structures:

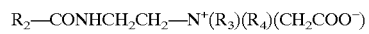

wherein: $R_2$ is chosen from, for example, alkyl radicals, acids of the formula $R_2$—COOH present in hydrolysed coconut oil, heptyl radicals, nonyl radicals, and undecyl radicals. $R_3$ is a beta-hydroxyethyl group and $R_4$ is a carboxymethyl group; and

wherein:

B is chosen from —$CH_2CH_2OX'$, C is chosen from —$(CH_2)_z$—Y', wherein z is a number equal to either 1 or 2;

X' is chosen from a —$CH_2CH_2$—COOH group and a hydrogen atom;

Y' is chosen from a —COOH group and a —$CH_2$—CHOH—$SO_3H$ radical;

$R_2'$ is chosen from alkyl radicals of acids $R_9$—COOH present in coconut oil and in hydrolysed linseed oil, alkyl radicals such as $C_7$, $C_9$, $C_{11}$ and $C_{13}$ alkyl radicals, $C_{17}$ alkyl radicals and their iso form, and unsaturated $C_{17}$ radicals.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

For example, cocoamphodiacetate is sold under the trade name Miranol® C2M concentrate by the company Rhodia Chimie.

(iv) Cationic Surfactant(s):

At least one cationic surfactant may be chosen, for example, from the following: primary, secondary and tertiary fatty amine salts, optionally polyoxyalkylenated; quaternary ammonium salts, such as tetraalkylammonium, alkylamidoalkyltrialkyl-ammonium, trialkylbenzylammonium, trialkylhydroxyalkylammonium and alkylpyridinium chlorides and bromides; imidazoline derivatives; and amine oxides of cationic nature.

The at least one surfactant may be present in an amount ranging from 0.01 to 40%, for example from 0.5 to 30% of the total weight of the composition.

Medium

A cosmetically acceptable medium may comprise, for example, at least one of the following: aqueous media comprising water; cosmetically acceptable organic solvents, such as alcohols, for example ethyl alcohol, isopropyl alcohol, benzyl alcohol and phenylethyl alcohol; glycols and glycol ethers, such as ethylene glycol monomethyl, monoethyl and monobutyl ethers, propylene glycol and its ethers, such as propylene glycol monomethyl ether, butylene glycol, dipropylene glycol; and alkyl ethers of diethylene glycol, such as diethylene glycol monoethyl and monobutyl ether. At least one cosmetically acceptable organic solvent may be present in concentrations ranging from 0.5 to 20%, and, for example from 2 to 10%, by weight relative to the total weight of the composition.

Modifiers

In another embodiment, the composition may further comprise at least one rheology modifier. The at least one rheology modifier may be chosen, for example, from cellulosic thickeners (hydroxyethylcellulose, hydroxypropylcellulose, carboxymethylcellulose, etc.), guar gum and its derivatives (hydroxypropylguar, etc.), gums of microbial origin (xanthan gum, scleroglucan gum, etc.), and synthetic thickeners, such as crosslinked homopolymers of acrylic acid and crosslinked homopolymers of acrylamidopropane-sulphonic acid.

In another embodiment, the compositions may further comprise at least one ionic or nonionic associative polymer chosen, for example, from the polymers sold under the names Pemulen® TR1 or TR2 by the company Goodrich, Salcare SC90® by the company Allied Colloids, Aculyn® 22, 28, 33, 44 or 46 by the company Rohm & Haas and Elfacos® T210 and T212 by Akzo. The at least one ionic or non-ionic associative polymer may be present in an amount ranging, for example from 0.01 to 10% by weight of the total weight of the composition.

According to another embodiment, the compositions may further comprise at least one cationic conditioning polymer or at least one amphoteric conditioning polymer, which is well-known in the art in the field of dyeing of human keratin fibres. The at least one cationic or amphoteric conditioning polymer may be from 0.01 to 10% by weight relative to the total weight of the composition, for example, from 0.05 to 5% and, for further example, from 0.1 to 3%.

Cationic Polymers

The phrase "cationic polymer" means, for example, any polymer comprising cationic groups and/or groups that can be ionized into cationic groups.

At least one cationic polymer may be chosen, for example, from any cationic polymers known to improve the cosmetic properties of the hair. The at least one cationic polymer is chosen from, for example, the polymers described in Patent Application EP-A-337 354, and French Patent Nos. FR-2 270 846, 2 383 660, 2 598 611, 2 470 596 and 2 519 863.

The at least one cationic polymer may be chosen, for example, from cationic polymers which comprise monomeric units comprising primary, secondary, tertiary and quaternary amine groups which may form part of the main polymer chain or which may be carried by a lateral substituent attached to the main polymer chain.

The at least one cationic polymer may have, for example, a number-average molecular mass ranging from 500 to $5 \times 10^6$, for example from $10^3$ to $3 \times 10^6$.

The at least one cationic polymer may be chosen, for example, from polymers of poly(quaternary ammonium), polymers of polyamino amide, and polymers of polyamine.

These are well-known products and are described, for example, in French Patent Nos. 2 505 348 and 2 542 997. The at least one cationic polymer may be chosen, for example, from the following:

(1) At least one homopolymer or at least one copolymer derived from acrylic and methacrylic esters and amides and comprising at least one of the units of formula (I), (II), (III) or (IV) below:

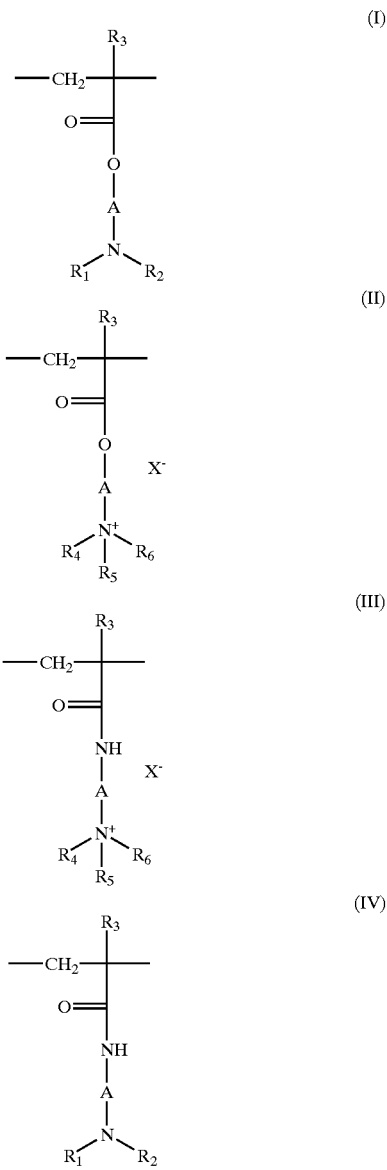

wherein:

$R_3$, which may be identical or different, is chosen from a hydrogen atom and a $CH_3$ radical;

A, which may be identical or different, is chosen from linear and branched alkyl groups of 1 to 6 carbon atoms, such as 2 or 3 carbon atoms, and hydroxyalkyl groups comprising 1 to 4 carbon atoms;

$R_4$, $R_5$ and $R_6$, which may be identical or different, are chosen from alkyl groups comprising from 1 to 18 carbon atoms, such as alkyl groups comprising from 1 to 6 carbon atoms, and a benzyl radical;

$R_1$ and $R_2$, which may be identical or different, are chosen from a hydrogen atom and alkyl groups comprising from 1 to 6 carbon atoms, such as a methyl group and a ethyl group;

$X^-$ is chosen from anions derived from inorganic and organic acids, such as a methosulphate anion, and halides, such as chloride and bromide.

At least one homopolymer or at least one copolymer of class (1) may further comprise at least one monomeric unit chosen from comonomers, such as acrylamides, methacrylamides, diacetoneacrylamides, acrylamides and methacrylamides substituted on the nitrogen with lower ($C_1$–$C_4$) alkyls, acrylic or methacrylic acids and esters thereof, vinyllactams such as vinylpyrrolidone and vinylcaprolactam, and vinyl esters.

The at least one homopolymer or the at least one copolymer of class (1) may be chosen, for example, from:

copolymers of acrylamide and of dimethylaminoethyl methacrylate quaternized with dimethyl sulphate and with a dimethyl halide, such as the product sold under the name Hercofloc by the company Hercules, the copolymers of acrylamide and of methacryloyloxyethyltrimethylammonium chloride described, for example, in Patent Application EP-A-080 976, and sold under the name Bina Quat P 100 by the company Ciba Geigy, the copolymers of acrylamide and of methacryloyloxyethyltrimethylammonium methosulphate sold under the name Reten by the company Hercules, quaternized and non-quaternized vinylpyrrolidone/dialkylaminoalkyl acrylate and methacrylate copolymers, such as the products sold under the name Gafquat by the company ISP, such as Gafquat 734 and Gafquat 755, and the products known as Copolymer 845, 958 and 937. These polymers, for example, are described in French Patent Nos. 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold, for example, under the name Styleze CC 10 by the company ISP, and quaternized vinylpyrrolidone/dimethylaminopropylmethacrylamide copolymers, such as the product sold under the name Gafquat HS 100 by the company ISP.

(2) At least one cellulose ether derivative chosen from, for example, cellulose ether derivatives comprising at least one quaternary ammonium group, described in French Patent No.1 492 597, such as polymers sold under the names JR (JR 400, JR 125 and JR 30M) or LR (LR 400, or LR 30M) by the company Union Carbide Corporation. These polymers are also defined in the CTFA dictionary as quaternary ammoniums of hydroxyethylcellulose that has reacted with an epoxide substituted by a trimethylammonium group.

(3) At least one cationic cellulose derivative chosen, for example, from cellulose copolymers and cellulose derivatives grafted with at least one water-soluble monomer of quaternary ammonium and described, for example, in U.S. Pat. No. 4,131,576, such as hydroxyalkylcelluloses, for example hydroxymethyl-, hydroxyethyl- or hydroxypropylcelluloses grafted, for example, with at least one salt chosen from methacryloylethyltrimethylammonium salts, methacrylamidopropyltrimethylammonium salts and dimethyldiallylammonium salts.

The at least one cationic cellulose derivative may be chosen, for example, from the products sold under the names Celquat L 200 and Celquat H 100 by the company National Starch.

(4) At least one cationic polysaccharide chosen, for example, from cationic polysaccharides described in U.S. Pat. Nos. 3,589,578 and 4,031,307, such as guar gums comprising at least one cationic trialkylammonium group. Guar gums modified with at least one salt (e.g., chloride) of 2,3-epoxypropyltrimethylammonium may also be chosen, for example.

The at least one cationic polysaccharide may be chosen, for example, from products sold under the trade names Jaguar C13 S, Jaguar C 15, Jaguar C 17 and Jaguar C162 by the company Meyhall.

(5) At least one polymers chosen, for example, from polymers comprising monomeric units of piperazinyl and of divalent alkylene and hydroxyalkylene radicals comprising straight and branched chains, optionally interrupted by oxygen, sulphur and nitrogen atoms and by aromatic and heterocyclic rings, and the oxidation and quaternization products of these polymers. Such polymers are described, for example, in French Patent Nos. 2 162 025 and 2 280 361.

(6) At least one water-soluble polyamino amide chosen, for example, from water-soluble polyamino amides prepared, for example, by polycondensation of acidic compounds with polyamines. The at least one water-soluble polyamino amide may be, for example, crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide, or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; At least one crosslinking agent may be present in an amount ranging from 0.025 to 0.35 mol per amine group of the polyamino amide. The at least one water-soluble polyamino amide may be, for example, alkylated or, if it comprises at least one tertiary amine function, it may be quaternized. Such polymers are described, for example, in French Patent Nos. 2 252 840 and 2 368 508.

(7) At least one polyamino amide derivative chosen, for example, from polyamino amide derivatives resulting from the condensation of polyalkylene polyamines with polycarboxylic acids followed by alkylation with difunctional agents. The at least one polyamino amide derivative may be chosen, for example, from adipic acid/diacylaminohydroxyalkyldialkylenetriamine polymers wherein at least one alkyl radical comprises from 1 to 4 carbon atoms, such as a methyl radical, ethyl radical and propyl radical. Such polymers are described, for example, in French Patent No. 1 583 363.

The at least one polyamino amide derivative may also be chosen, for example, from adipic acid/dimethylaminohydroxypropyl/diethylenetriamine polymers sold under the name Cartaretine F, F4, or F8 by the company Sandoz.

(8) At least one polymer chosen, for example, from polymers obtained by reaction of polyalkylene polyamines comprising two primary amine groups and at least one secondary amine group with at least one dicarboxylic acid chosen from diglycolic acid and saturated aliphatic dicarboxylic acids comprising from 3 to 8 carbon atoms. The molar ratio between the polyalkylene polyamine and the dicarboxylic acid may range, for example, from 0.8:1 to 1.4:1; the polyamino amide resulting therefrom may be reacted with epichlorohydrin in a molar ratio of epichlorohydrin relative to the secondary amine group of the polyamino amide of from 0.5:1 to 1.8:1. Such polymers are described in, for example, U.S. Pat. Nos. 3,227,615 and 2,961,347.

At least one polymer of this type may be chosen, for example, from polymers sold under the name Hercosett 57 by the company Hercules Inc., and under the name PD 170 or Delsette 101 by the company Hercules in the case of adipic acid/epoxypropyl/diethylenetriamine copolymers.

(9) At least one cyclopolymer chosen, for example, from cyclopolymers of alkyldiallylamine and of dialkyldiallylammonium, such as the homopolymers or copolymers comprising, as main constituent of the chain, at least one monomeric unit of the formula (V) or (VI):

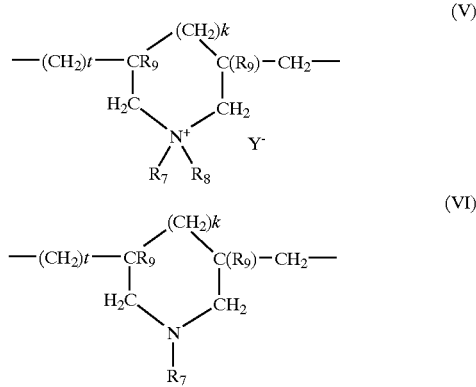

wherein k and t are 0 or 1, the sum k+t being equal to 1; $R_9$ is chosen from a hydrogen atom and a methyl radical; $R_7$ and $R_8$, which may be identical or different, may be chosen from alkyl groups comprising from 1 to 8 carbon atoms; hydroxyalkyl groups, wherein alkyl groups have, for example, from 1 to 5 carbon atoms; lower ($C_1$–$C_4$) amidoalkyl groups; $R_7$ and $R_8$ may also comprise, together with the nitrogen atom to which they are attached, heterocyclic groups, such as piperidyl or morpholinyl; $R_7$ and $R_8$, which may be identical or different, may also be chosen from alkyl groups comprising from 1 to 4 carbon atoms; $Y^-$ is chosen from anions, such as bromide, chloride, acetate, borate, citrate, tartrate, bisulphate, bisulphite, sulphate and phosphate. These polymers are described, for example, in French Patent No. 2 080 759 and in its certificate of addition 2 190 406.

The at least one cyclopolymer may be chosen, for example, from the dimethyldiallylammonium chloride homopolymer sold under the name Merquat 100 by the company Calgon (and its homologues of low weight-average molecular mass) and copolymers of diallyldimethylammonium chloride and of acrylamide, sold under the name Merquat 550.

(10) At least one quaternary diammonium polymer comprising monomeric units of the formula:

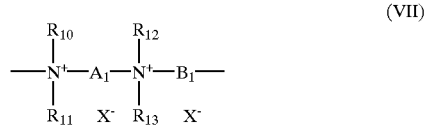

wherein formula (VII):

$R_{10}$, $R_{11}$, $R_{12}$ and $R_{13}$, which may be identical or different, may be chosen from aliphatic, alicyclic or arylaliphatic radicals comprising from 1 to 20 carbon atoms and lower hydroxyalkylaliphatic radicals; $R_{10}$, $R_{11}$, $R_{12}$ and $R_{13}$, together or separately, constitute, with the nitrogen atoms to which they are attached, heterocycles optionally comprising a second heteroatom other than nitrogen; $R_{10}$, $R_{11}$, $R_{12}$ and $R_{13}$ may also be chosen from linear and branched $C_1$–$C_6$ alkyl radicals substituted with nitrile groups, ester groups, acyl groups, amide groups, and groups of the formulae —CO—O—$R_{14}$—D and —CO—NH—$R_{14}$—D, wherein $R_{14}$ is chosen from alkylenes and D is chosen from quaternary ammonium groups;

$A_1$ and $B_1$ are chosen from polymethylene groups comprising from 2 to 20 carbon atoms, which may be linear and branched, saturated and unsaturated, and which may comprise, linked to and intercalated in the main chain, at least one aromatic ring and at least one oxygen atom and at least one sulphur atom and sulphoxide, sulphone, disulphide, amino, alkylamino, hydroxyl, quaternary ammonium, ureido, amide and ester groups, and $X^-$ is chosen from anions derived from inorganic and organic acids;

$A_1$, $R_{10}$ and $R_{12}$ may comprise, with the two nitrogen atoms to which they are attached, a piperazine ring; in addition, if $A_1$ is chosen from linear and branched, saturated and unsaturated alkylenes and hydroxyalkylene radicals, $B_1$ may also be chosen from groups of the formula —$(CH_2)_n$—CO-D-OC—$(CH_2)_n$— wherein n ranges from 1 to 100, such as from 1 to 50, and D is chosen from:

a) glycol residues of the formula: —O-Z-O—, where Z is chosen from linear and branched hydrocarbon radicals and groups of the following formulae:

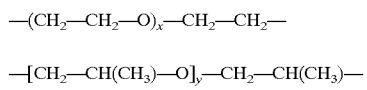

where x and y are integers ranging from 1 to 4, representing defined and unique degrees of polymerization and numbers from 1 to 4 representing average degrees of polymerization;

b) bis-secondary diamine residues, such as piperazine derivatives;

c) bis-primary diamine residues of formula: —NH—Y—NH—, where Y is chosen from linear and branched hydrocarbon radicals and divalent radicals

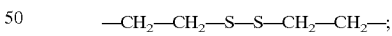

d) ureylene groups of formula: —NH—CO—NH—.

$X^-$ may be chosen, for example, from anions, such as chloride or bromide.

These polymers, for example, may have a number-average molecular mass ranging from 1000 to 100,000.

Polymers of this type are described, for example, in French Patent Nos. 2 320 330, 2 270 846, 2 316 271, 2 336 434 and 2 413 907, and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

The at least one quaternary diammonium polymer may also be chosen, for example, from polymers comprising monomeric units of the formula (VIII) below:

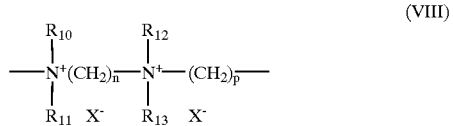

(VIII)

wherein $R_{10}$, $R_{11}$, $R_{12}$ and $R_{13}$, which may be identical or different, are chosen from alkyl and hydroxyalkyl radicals comprising from 1 to 4 carbon atoms, n and p are integers ranging from 2 to 20, and $X^-$ is chosen from anions derived from mineral acids and organic acids.

(11) At least one poly(quaternary ammonium) polymer chosen from poly(quaternary ammonium) polymers composed of repeating units of formula (IX):

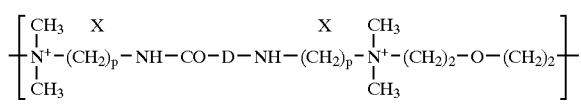

(IX)

wherein p is an integer ranging from 1 to 6, D can be non-existent or can represent a group of formula $-(CH_2)_r-CO-$, wherein r is a number equal to 4 or 7, and $X^-$ comprises at least one anion.

Such polymers may be prepared by the processes disclosed in U.S. Pat. Nos. 4,157,388, 4,702,906 and 4,719,282. They are also described in European Patent Application No. EP-A-122 324.

The at least one quaternary diammonium polymer may also be chosen, for example, from the products Mirapol A 15, Mirapol AD1, Mirapol AZ1 and Mirapol 175, which are sold by the company Miranol.

(12) At least one quaternary polymer chosen from quaternary polymers of vinylpyrrolidone and of vinylimidazole, such as the products sold under the names Luviquat FC 905, FC 550 and FC 370 by the company BASF.

(13) At least one polyamine chosen from polyamines, such as Polyquart H sold by Henkel, referenced under the name Polyethylene glycol (15) tallow polyamine in the CTFA dictionary.

(14) At least one crosslinked methacryloyloxy($C_1$–$C_4$)alkyltri($C_1$–$C_4$)alkyl-ammonium salt polymer chosen from polymers obtained by homopolymerization of dimethylaminoethyl methacrylate quaternized with methyl chloride, and by copolymerization of acrylamide with dimethylaminoethyl methacrylate quaternized with methyl chloride, the homo- and copolymerizations being followed by crosslinking with a compound comprising olefinic unsaturation, such as methylenebisacrylamide. The at least one crosslinked methacryloyloxy($C_1$–$C_4$)alkyltri($C_1$–$C_4$)alkylammonium salt polymer may comprise, for example, a crosslinked acrylamide/methacryloyloxyethyltrimethylammonium chloride copolymer (20/80 by weight) in the form of a dispersion comprising 50% by weight of said copolymer in mineral oil. This dispersion is sold, for example, under the name Salcare® SC 92 by the company Allied Colloids. The at least one crosslinked methacryloyloxy($C_1$–$C_4$)alkyltri($C_1$–$C_4$) alkylammonium salt polymer may further comprise, for example, a crosslinked methacryloyloxyethyltrimethylammonium chloride homopolymer comprising about 50% by weight of the homopolymer in mineral oil or in a liquid ester. These dispersions are sold, for example, under the names Salcare® SC 95 and Salcare® SC 96 by the company Allied Colloids.

At least one cationic polymer may further be chosen from, for example, polyalkyleneimines, such as polyethyleneimines, polymers comprising vinylpyridine and vinylpyridinium monomeric units, condensates of polyamines and of epichlorohydrin, quaternary polyureylenes and chitin derivatives.

The at least one cationic polymer may be chosen from, for example, the polymers of classes (1), (9), (10), (11) and (14). The at least one cationic polymer may also be chosen from, for example, polymers with repeating units of formulae (W) and (U) below:

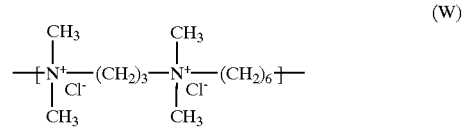

(W)

wherein the molecular weight, determined by gel permeation chromatography, for example, ranges from 9500 to 9900;

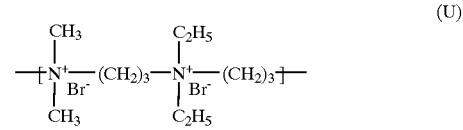

(U)

wherein the molecular weight, determined by gel permeation chromatography is, for example, 1200.

Amphoteric Polymer

The at least one amphoteric polymer may be chosen from, for example, polymers comprising units K and M, which can be identical or different, distributed randomly in the polymer chain, where K may comprise a unit derived from a monomer comprising at least one nitrogen atom, and where M may comprise a unit derived from an acidic monomer comprising at least one group chosen from carboxylic groups and sulphonic groups, K and M may be chosen, for example, from groups derived from carboxybetaine or sulphobetaine zwitterionic monomers;

K and M may also comprise a cationic polymer chain comprising at least one primary, secondary, tertiary or quaternary amine group, wherein at least one amine group has a carboxylic group or sulphonic group connected via a hydrocarbon radical. K and M may also comprise part of a chain of a polymer comprising at least one α,β-dicarboxylic ethylene unit wherein at least one carboxylic group has been made to react with a polyamine comprising at least one primary amine group or at least one secondary amine groups.

The at least one amphoteric polymer may be chosen, for example, from the following polymers:

(1) At least one polymer chosen from polymers resulting from the copolymerization of monomers derived from vinyl compounds bearing at least one carboxylic group, such as acrylic acid, methacrylic acid, maleic acid, alpha-chloroacrylic acid, and basic monomers derived from at least one substituted vinyl compound comprising at least one basic atom, such as dialkylaminoalkyl methacrylates and acrylates, dialkylaminoalkylmethacrylamides and -acrylamides. Such compounds are described in U.S. Pat. No. No. 3,836,537. One such compound may comprise, for example, sodium acrylate/acrylamidopropyltrimethylammonium chloride copolymer sold under the name Polyquart KE 3033 by the company Henkel.

The vinyl compound may be a dialkyldiallylammonium salt, such as dimethyldiallylammonium chloride. The copolymers of acrylic acid and of the latter monomer are sold, for example, under the names Merquat 280, Merquat 295 and Merquat Plus 3330 by the company Calgon.

(2) At least one polymer comprising at least one monomeric unit derived from:

a) at least one monomer chosen from acrylamides and methacrylamides substituted on the nitrogen by an alkyl radical, b) at least one acidic comonomer comprising at least one reactive carboxylic group, and c) at least one basic comonomer chosen, for example, from esters comprising primary, secondary, tertiary and quaternary amine substituents of acrylic and methacrylic acids and the product of quaternization of dimethylaminoethyl methacrylate with dimethyl and diethyl sulphate.

The at least one N-substituted acrylamide or at least one methacrylamide may be chosen from, for example, groups wherein the alkyl radicals comprise from 2 to 12 carbon atoms, such as N-ethylacrylamide, N-tert-butylacrylamide, N-tert-octylacrylamide, N-octylacrylamide, N-decylacrylamide, N-dodecylacrylamide and the corresponding methacrylamides.

The at least one acidic comonomer may be chosen from, for example, acrylic acid, methacrylic acid, crotonic acid, itaconic acid, maleic acid and fumaric acid and alkyl monoesters, comprising 1 to 4 carbon atoms, of maleic and fumaric acids and anhydrides.

The at least one comonomer may be chosen from, for example, aminoethyl, butylaminoethyl, N,N'-dimethylaminoethyl and N-tert-butylaminoethyl methacrylates.

The at least one copolymer may be chosen from, for example, a copolymer whose CTFA (4th edition, 1991) name is octylacrylamide/acrylates/butylaminoethyl methacrylate copolymer, and the products sold under the name Amphomer or Lovocryl 47 by the company National Starch.

(3) At least one crosslinked or at least one alkylated polyamino amide chosen from crosslinked and alkylated polyamino amides partially or totally deriving from polyamino amides of general formula:

$$-[-CO-R_{19}-CO-Z-]-\quad\quad (X)$$

wherein $R_{19}$ is chosen from divalent radicals derived from saturated dicarboxylic acids, mono- and dicarboxylic aliphatic acids comprising at least one ethylenic double bond, at least one ester of a lower alkanol, comprising 1 to 6 carbon atoms, of these acids and radicals deriving from the addition of any one of said acids with bis(primary) and bis(secondary) amines, and Z is chosen from bis(primary), mono- and bis(secondary) polyalkylene-polyamine radicals, for example:

a) ranging from 60 to 100 mol %, the radicals

where x=2 and p=2 or 3, or x=3 and p=2, these radicals being derived from diethylenetriamine, from triethylenetetraamine, and from dipropylenetriamine;

b) in amounts ranging from 0 to 40 mol %, the radicals (XI) above wherein x=2 and p=1 and which are derived from ethylenediamine, or the radicals deriving from piperazine:

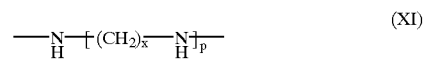

c) in amounts ranging from 0 to 20 mol %, the —NH—$(CH_2)_6$—NH— radicals deriving from hexamethylenediamine, these polyamino amines being crosslinked by addition of difunctional crosslinking agents chosen from epihalohydrins, diepoxides, dianhydrides and bis-unsaturated derivatives, using from 0.025 to 0.35 mol of crosslinking agent per amine group of the polyamino amides and alkylated by the action of acrylic acid, chloroacetic acid and alkane sultones, and salts thereof.

The at least one saturated carboxylic acid is chosen, for example, from acids comprising 6 to 10 carbon atoms, such as adipic acid, 2,2,4-trimethyladipic acid and 2,4,4-trimethyladipic acid, terephthalic acid, acids comprising at least one ethylenic double bond, such as acrylic acid, methacrylic acid and itaconic acid.

The at least one alkane sultone used in the alkylation is chosen, for example, from propane and butane sultones. The at least one salt of at least one alkylating agent is chosen from, for example, the sodium and potassium salts.

(4) At least one polymer comprising at least one zwitterionic monomeric unit of formula:

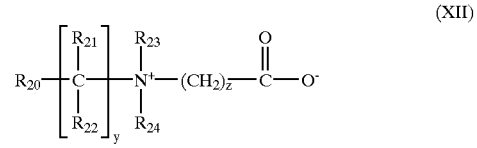

wherein $R_{20}$ is chosen from polymerizable unsaturated groups, such as acrylate groups, methacrylate groups, acrylamide groups and methacrylamide groups; y and z, which may be identical or different, are chosen from integers ranging from 1 to 3; $R_{21}$ and $R_{22}$, which may be identical or different, are chosen from a hydrogen atom, methyl group, ethyl group and propyl group; $R_{23}$ and $R_{24}$, which may be identical or different, are chosen from a hydrogen atom and alkyl radicals, such that the sum of the carbon atoms in $R_{23}$ and $R_{24}$ does not exceed 10.

At least one polymer may also comprise monomeric units chosen from non-zwitterionic monomers such as dimethyl or diethylaminoethyl acrylate and methacrylate and alkyl acrylates and methacrylates, acrylamides and methacrylamides and vinyl acetate.

At least one polymer comprising at least one zwitterionic monomeric unit may comprise, for example, the copolymer of butyl methacrylate/dimethyl-carboxymethylammonio-ethyl methacrylate, such as the product sold under the name Diaformer Z301 by the company Sandoz.

(5) At least one polymer derived from chitosan comprising monomeric units of the following formulae (XIII), (XIV) and (XV):

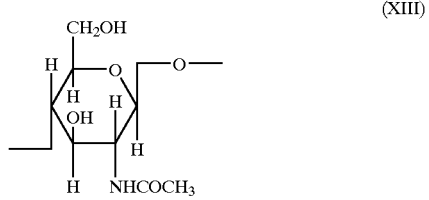

-continued

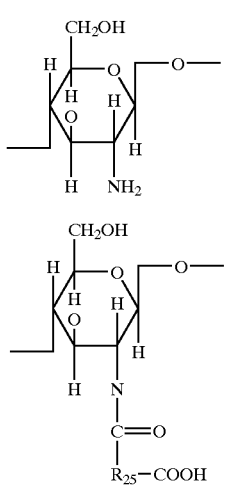

(XIV)

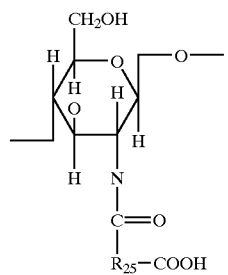

(XV)

the unit (XIII) being present in proportions ranging from 0 to 30%, the unit (XIV) in proportions ranging from 5 to 50%, and the unit (XV) in proportions ranging from 30 to 90%; in unit (XV), $R_{25}$ is chosen from radicals of formula:

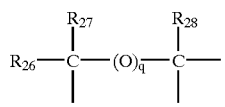

wherein q=0 or 1;

if q=0, $R_{26}$, $R_{27}$ and $R_{28}$, which may be identical or different, are chosen from a hydrogen atom, methyl residues, hydroxyl residues, acetoxy residues, amino residues, monoalkylamine residues, and dialkylamine residues which are optionally interrupted by nitrogen atoms and optionally substituted with amines, hydroxyl, carboxyl, alkylthio and sulphonic groups, alkylthio residues wherein at least one alkyl group bears an amino residue, at least one of the radicals $R_{26}$, $R_{27}$ and $R_{28}$ being a hydrogen atom;

or if q=1, $R_{26}$, $R_{27}$ and $R_{28}$, which may be identical or different, are chosen from a hydrogen atom, and acid and base salts formed by these compounds.

(6) At least one polymer chosen from polymers derived from the N-carboxyalkylation of chitosan, such as N-carboxymethylchitosan and N-carboxybutylchitosan sold under the name Evalsan by the company Jan Dekker.

(7) At least one polymer of the general formula (XI), such as those described, for example, in French Patent No. 1 400 366:

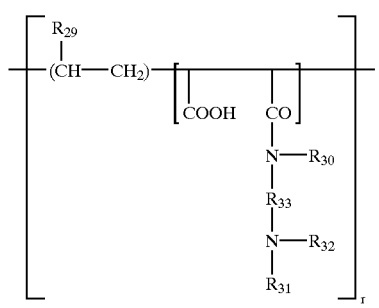

(XVI)

wherein $R_{29}$ is chosen from a hydrogen atom, $CH_3O$, $CH_3CH_2O$ and phenyl radicals, $R_{30}$ is chosen from a hydrogen atom and lower alkyl radicals, such as methyl and ethyl, $R_{31}$ is chosen from a hydrogen atom or lower alkyl radicals, such as methyl and ethyl, $R_{32}$ is chosen from lower alkyl radicals, such as methyl and ethyl and radicals of the formula: $-R_{33}-N(R_{31})_2$, $R_{33}$ chosen from $-CH_2-CH_2-$, $-CH_2-CH_2-CH_2-$ and $-CH_2-CH(CH_3)-$ groups, $R_{31}$ is chosen from a hydrogen atom and lower alkyl radicals, such as methyl and ethyl, and also the higher homologues of theses radicals comprising up to 6 carbon atoms;

r is an integer chosen such that the molecular weight ranges from 500 to 6,000,000, such as from 1000 to 1,000,000.

(8) At least one amphoteric polymer chosen from amphoteric polymers of the type -D-X-D-X- selected from:

a) polymers obtained by the action of chloroacetic acid or sodium chloroacetate on compounds comprising at least one unit of formula:

D-X-D-X-D (XVII)

wherein D is the following radical:

and X is chosen from E and E', E and E', which may be identical or different, are chosen from divalent alkylene radicals with straight and branched chains comprising up to 7 carbon atoms in the main chain, which are unsubstituted and substituted by hydroxyl groups and which can comprise, in addition to the oxygen, nitrogen and sulphur atoms, 1 to 3 aromatic and heterocyclic rings; the oxygen, nitrogen and sulphur atoms being present in a form chosen from of ether, thioether, sulphoxide, sulphone, sulphonium, alkylamine or alkenylamine groups, hydroxyl, benzylamine, amine oxide, quaternary ammonium, amide, imide, alcohol, ester and urethane groups;

b) polymers of formula:

-D-X-D-X- (XVIII)

wherein D denotes a radical

and X is chosen from E and E' and at least once being E'; E has the meaning given above and E' is chosen from divalent alkylene radicals with straight and branched chains comprising up to 7 carbon atoms in the main chain, which are optionally substituted with at least one hydroxyl radical and comprising at least one nitrogen atom substituted with an alkyl chain, which is optionally interrupted by at least one oxygen atom and further comprising at least one functional group chosen from carboxyl functional groups and hydroxyl functional groups which are betainized by reaction with chloroacetic acid or sodium chloroacetate.

(9) At least one copolymer chosen from $(C_1-C_5)$alkyl vinyl ether/maleic anhydride copolymers partially modified by semiamidation with at least one N,N-dialkylaminoalkylamine, such as N,N-dimethylaminopropylamine, and by semiesterification with at least one N,N-dialkanolamine. These copolymers may further comprise other vinyl comonomers, such as vinylcaprolactam.

The at least one amphoteric polymer may be chosen, for example, from class (1).

In another embodiment, the composition may further comprise an effective amount of at least one agent chosen from, for example, agents well-known in the art of direct or oxidation dyeing, such as various adjuvants, such as sequestrants, such as EDTA and etidronic acid, UV filters, waxes, volatile and nonvolatile, cyclic and linear and branched, organically modified and unmodified silicones, preservatives, ceramides, pseudoceramides, plant oils, mineral oils and synthetic oils, vitamins and provitamins, such as panthenol, and opacifiers.

In another embodiment, the composition may further comprise, for example, at least one reducing agent or at least one antioxidant. The at least one reducing agent or at least one antioxidant may be chosen, for example, from sodium sulphite, thioglycolic acid, thiolactic acid, sodium bisulphite, dehydroascorbic acid, hydroquinone, 2-methylhydroquinone, tert-butylhydroquinone and homogentisic acid. The at least one reducing agent or at least one antioxidant may be present in an amount ranging from, for example, 0.05 to 3% by weight, relative to the total weight of the composition.

In a further embodiment, a person having ordinary skill in the art may select at least one compound, such that the composition further comprises another adjuvant.

In another embodiment, the at least one oxidizing agent may be chosen, for example, from urea peroxide, alkali metal bromates and ferricyanides and persalts, such as perborates and persulphates. The at least one oxidizing agent may comprise, for example, hydrogen peroxide. The at least one oxidizing agent may further comprise, for example, a solution of oxygenated water whose titre may vary, for example, from 1 to 40 volumes, such as from 5 to 40 volumes.

The at least one oxidizing agent may also be chosen, for example, from redox enzymes, such as laccases, peroxidases and 2-electron oxidoreductases (such as uricase), in the presence of their respective donor or cofactor where appropriate.

In another embodiment, the pH of a ready-to-use composition applied to human keratin fibres, such as hair, [composition resulting from the mixing of the dyeing composition and oxidizing composition] may, for example, range from 4 to 11. The pH may, for example, range from 6 to 10, and may be adjusted to the desired value using at least one acidifying agent or at least one basifying agent, which are well known in the art of dyeing keratin fibres.

The at least one basifying agent may be chosen, for example, from aqueous ammonia, alkali metal carbonates, alkanolamines such as mono-, di- and triethanolamines and also derivatives thereof, oxyethylenated and oxypropylenated hydroxyalkylamines and ethylenediamines, sodium hydroxide, potassium hydroxide and the compounds of formula (VI) below:

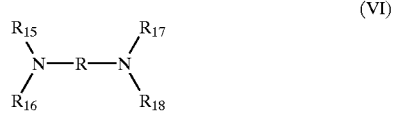

(VI)

wherein R is chosen from propylene residues optionally substituted by hydroxyl groups and $C_1$–$C_4$ alkyl radicals; $R_{15}$, $R_{16}$, $R_{17}$ and $R_{18}$, which may be identical or different, are chosen from a hydrogen atom and $C_1$–$C_4$ alkyl radicals and $C_1$–$C_4$ hydroxyalkyl radicals.

The at least one acidifying agent may be chosen, for example, from mineral acids and organic acids, such as hydrochloric acid, orthophosphoric acid, carboxylic acids, such as tartaric acid, citric acid and lactic acid, and sulphonic acids.

In another embodiment, a dyeing method comprises, for example, applying the composition or ready-to-use composition (produced extemporaneously at the time of use from the at least one colouring composition and the at least one oxidizing composition described above) to the wet or dry human keratin fibres, such as hair, and leaving the composition to act for a time ranging, for example, from 1 to 60 minutes, such as from 10 to 45 minutes, optionally rinsing the fibres, optionally washing the fibres with shampoo, optionally rinsing them again, and optionally drying them.

Illustrative, non-limiting examples follow.

EXAMPLE 1

The following direct dyeing composition was prepared:
Expressed in Grams of Active Substance

| | |
|---|---|
| Direct dye: Basic Blue 99 | 0.1 |
| Polydimethylsiloxane of formula (II), sold under the name SLM 28020 ® by Wacker | 2 |
| Ethanol | 20 |
| Hydroxypropylated guar gum: Jaguar HP60 ® sold by Aqaulon | 1 |
| C8–C10 alkyl polyglucoside in aqueous solution, comprising 60% active substance: Oramix CG110 ® sold by SEPPIC | 8 |
| 2-Amino-2-methyl-1-propanol qs pH | 7.5 |
| Demineralized water qs | 100 |

This composition was applied to locks of natural grey hair comprising 90% white hairs for 30 minutes.

The hair was subsequently rinsed, washed with a standard shampoo and then dried.

A blue shade was obtained which was highly resistant to several shampooings.

Moreover, the cosmetic condition of the fibres was highly satisfactory.

EXAMPLE 2

The following oxidation dyeing composition was prepared:
Expressed in Grams of Active Substance

| | |
|---|---|
| Paraphenylenediamine | 0.108 |
| 2-Methyl-5-aminophenol | 0.123 |
| Polydinethylsiloxane of formula (I), provided under the name Belsil ADM 652 ® by Wacker | 2 |
| Ethanol | 20 |
| C8–C10 alkyl polyglucoside in aqueous solution, comprising 60% active substance: Oramix CG110 ® sold by SEPPIC | 3.6 |
| Benzyl alcohol | 2 |
| Polyethylene glycol comprising 8 mol of ethylene oxide | 3 |
| Sodium metabisulphite in aqueous solution, comprising 35% active substance | 0.227 |
| Pentasodium salt of diethylenetriaminepentaacetic acid | 0.48 |
| Aqueous ammonia comprising 20% $NH_3$ | 6.8 |
| Demineralized water qs | 100 |

This composition was mixed, weight for weight, with 20-volume hydrogen peroxide. The final pH of the mixture was 9.5.

The mixture was then applied to grey hair comprising 90% white hairs and was left to act for 30 minutes.

The hair was subsequently washed with a standard shampoo and then rinsed with water and dried.

The hair was dyed in a mauvish red shade which was resistant to several shampooings, and the fibres exhibited a highly satisfactory cosmetic condition.

What is claimed is:

1. A composition for dyeing keratin fibres comprising, in a cosmetically acceptable medium, at least one dye chosen from direct dyes and oxidation dyes, and further comprising at least one aminosilicone chosen from formula (I) and (II):

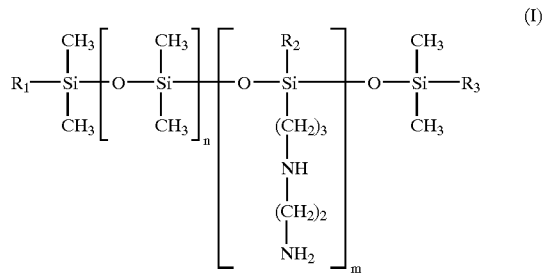

wherein:
   m and n are numbers with a sum (n+m) ranging from 1 to 1000,
   n is a number ranging from 0 to 999, and m is a number ranging from 1 to 1000;
   $R_1$, $R_2$ and $R_3$, which may be identical or different, are chosen from a hydroxyl radical and $C_1$–$C_4$ alkoxy radicals, at least one of the radicals $R_1$ to $R_3$ being an alkoxy radical;

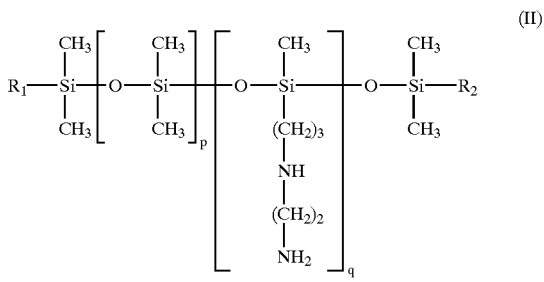

wherein:
   p and q are numbers with a sum (p+q) ranging from 1 to 1000,
   p is a number ranging from 0 to 999, and q is a number ranging from 1 to 1000;
   $R_1$ and $R_2$, which are different, are chosen from hydroxyl radicals and $C_1$–$C_4$ alkoxy radicals, at least one of the radicals $R_1$ and $R_2$ being an alkoxy radical.

2. The composition according to claim 1, wherein the keratin fibres are hair.

3. The composition according to claim 1, wherein the sum (n+m) ranges from 50 to 250.

4. The composition according to claim 3, wherein the sum (n+m) ranges from 100 to 200.

5. The composition according to claim 1, wherein n ranges from 49 to 249.

6. The composition according to claim 5, wherein n ranges from 125 to 175.

7. The composition according to claim 1, wherein m ranges from 1 to 10.

8. The composition according to claim 7, wherein m ranges from 1 to 5.

9. The composition according to claim 1, wherein the sum (p+q) ranges from 50 to 350.

10. The composition according to claim 9, wherein the sum (p+q) ranges from 150 to 250.

11. The composition according to claim 1, wherein p ranges from 49 to 349.

12. The composition according to claim 11, wherein p ranges from 159 to 239.

13. The composition according to claim 1, wherein q ranges from 1 to 10.

14. The composition according to claim 13, wherein q ranges from 1 to 5.

15. The composition according to claim 1, wherein the $C_1$–$C_4$ alkoxy radical is a methoxy radical.

16. The composition according to claim 1, wherein the at least one aminosilicone is chosen from formula (I) and has a hydroxy/alkoxy molar ratio ranging from 0.2:1 to 0.4:1.

17. The composition according to claim 1, wherein the at least one aminosilicone is chosen from formula (I) and has a hydroxy/alkoxy molar ratio ranging from 0.25:1 to 0.35:1.

18. The composition according to claim 1, wherein the at least one aminosilicone is chosen from formula (I) and has a hydroxy/alkoxy molar ratio being 0.3:1.

19. The composition according to claim 1, wherein the at least one aminosilicone is chosen from formula (II) and has a hydroxy/alkoxy molar ratio ranging from 1:0.8 to 1:1.1.

20. The composition according to claim 1, wherein the at least one aminosilicone is chosen from formula (II) and has a hydroxy/alkoxy molar ratio ranging from 1:0.9 to 1:1.

21. The composition according to claim 1, wherein the at least one aminosilicone is chosen from formula (II) and has a hydroxy/alkoxy molar ratio of 1:0.95.

22. The composition according to claim 1, wherein the at least one aminosilicone is chosen from formula (I) and has a weight-average molecular mass ranging from 2000 to 1 000 000.

23. The composition according to claim 22, wherein the at least one aminosilicone has a weight-average molecular mass ranging from 3500 to 200 000.

24. The composition according to claim 1, wherein the at least one aminosilicone is chosen from formula (II) and has a weight-average molecular mass ranging from 2000 to 200 000.

25. The composition according to claim 24, wherein the at least one aminosilicone has a weight-average molecular mass ranging from 5000 to 100 000.

26. The composition according to claim 25, wherein the at least one aminosilicone has a weight-average molecular mass ranging from 10 000 to 50 000.

27. The composition according to claim 1, wherein the at least one aminosilicone is in the form of an oil-in-water emulsion and further comprises at least one surfactant.

28. The composition according to claim 27, wherein the at least one surfactant is chosen from cationic surfactants and nonionic surfactants.

29. The composition according to claim 27, wherein the particle size of the at least one aminosilicone in the emulsion ranges from 3 to 500 nanometres.

30. The composition according to claim 29, wherein the particle size of the at least one aminosilicone in the emulsion ranges from 5 to 60 nanometres.

31. The composition according to claim 30, wherein the particle size of the at least one aminosilicone in the emulsion ranges from 10 to 50 nanometres.

32. The composition according to claim 1, wherein the at least one aminosilicone is chosen such that a contact angle with water of a hair treated with a composition comprising 2% AS (active substance) of the at least one aminosilicone ranges from 90 to 180°.

33. The composition according to claim 32, wherein the at least one aminosilicone is chosen such that the contact angle with water of a hair treated with a composition comprising 2% AS (active substance) of the at least one aminosilicone ranges from 90 to 130°.

34. The composition according to claim 1, wherein the at least one aminosilicone is chosen such that a contact angle of a hair treated with the composition ranges from 90 to 180°.

35. The composition according to claim 1, wherein the at least one aminosilicone is present in an amount ranging from 0.01 to 20% by weight, relative to the total weight of the composition.

36. The composition according to claim 35, wherein the at least one aminosilicone is present in an amount ranging from 0.1 to 15% by weight, relative to the total weight of the composition.

37. The composition according to claim 36, wherein the at least one aminosilicone is present in an amount ranging from 0.5 to 10% by weight, relative to the total weight of the composition.

38. The composition according to claim 1, wherein the at least one oxidation dye is chosen from oxidation bases and couplers.

39. The composition according to claim 38, wherein the at least one oxidation dye comprises at least one oxidation base.

40. The composition according to claim 39, wherein the at least one oxidation base is chosen from ortho- and para-phenylenediamines, double bases, ortho- and para-aminophenols, heterocyclic bases, and the acid addition salts of these compounds.

41. The composition according to claim 40, wherein at least one para-phenylenediamine is chosen from the compounds of structure (III):

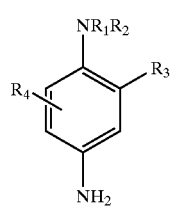

(III)

wherein:
$R_1$ is chosen from a hydrogen atom and $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$) alkyl radicals, $C_1$–$C_4$ alkyls substituted by at least one nitrogenous group, and phenyl and 4-aminophenyl radicals;
$R_2$ is chosen from a hydrogen atom and $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$) alkyl radicals, and $C_1$–$C_4$ alkyl radicals substituted by at least one nitrogenous group;
$R_1$ and $R_2$ may comprise, with the nitrogen atom to which they are attached, a 5- or 6-membered nitrogenous heterocycle optionally substituted by at least one group chosen from alkyl groups, a hydroxyl group, and ureido groups;
$R_3$ is chosen from a hydrogen atom, halogen atoms, $C_1$–$C_4$ alkyl radicals, sulpho radicals, carboxyl radicals, $C_1$–$C_4$ monohydroxyalkyl radicals, $C_1$–$C_4$ hydroxyalkoxy radicals, $C_1$–$C_4$ acetylaminoalkoxy radicals, $C_1$–$C_4$ mesylaminoalkoxy radicals, and $C_1$–$C_4$ carbamoylaminoalkoxy radicals; and
$R_4$ is chosen from a hydrogen atom, halogen atoms, and $C_1$–$C_4$ alkyl radicals.

42. The composition according to claim 41, wherein $R_3$ is a chlorine atom.

43. The composition according to claim 40, wherein the double bases are chosen from the compounds of formula (IV):

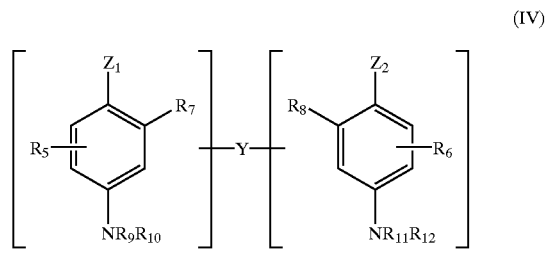

(IV)

wherein:
$Z_1$ and $Z_2$, which may be identical or different, are chosen from hydroxyl and —$NH_2$ radicals, which may be substituted by at least one $C_1$–$C_4$ alkyl radical or by a linking arm Y;
the linking arm Y is chosen from alkylene chains comprising from 1 to 14 carbon atoms, which are linear or branched and may be interrupted or terminated by at least one nitrogenous group or by at least one heteroatom, and which is optionally substituted by at least one radical chosen from hydroxyl radicals and $C_1$–$C_6$ alkoxy radicals;
$R_5$ and $R_6$, which may be identical or different, are chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, and a linking arm Y;
$R_7$, $R_8$, $R_9$, $R_{10}$, $R_{11}$ and $R_{12}$, which may be identical or different, are chosen from a hydrogen atom, a linking arm Y, and $C_1$–$C_4$ alkyl radicals;
with the proviso that the compounds of formula (IV) contain only one linking arm Y per molecule.

44. The composition according to claim 43, wherein the at least one heteroatom is chosen from an oxygen atom, a sulphur atom, and a nitrogen atom.

45. The composition according to claim 40, wherein the para-aminophenols are chosen from the compounds of formula (V):

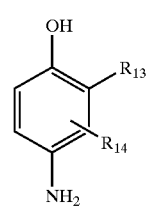

(V)

wherein:
$R_{13}$ is chosen from a hydrogen atom, halogen atoms, $C_1$–$C_4$ alkyl radicals, $C_1$–$C_4$ monohydroxyalkyl radicals, ($C_1$–$C_4$)alkoxy($C_1$–$C_4$)alkyl radicals, $C_1$–$C_4$ aminoalkyl radicals, and $C_1$–$C_4$ hydroxy($C_1$–$C_4$) alkylaminoalkyl radicals; and $R_{14}$ is chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, $C_1$–$C_4$ cyanoalkyl radicals, and ($C_1$–$C_4$)alkoxy($C_1$–$C_4$)alkyl radicals.

46. The composition according to claim 45, wherein $R_{13}$ is a fluorine atom.

47. The composition according to claim 40, wherein the heterocyclic bases are chosen from pyridine derivatives, pyrimidine derivatives, and pyrazole derivatives.

48. The composition according to claim 39, wherein the at least one oxidation base is present in an amount ranging from 0.0005 to 12% by weight, relative to the total weight of the composition.

49. The composition according to claim 38, wherein the couplers are chosen from meta-phenylenediamines, meta-aminophenols, meta-diphenols, heterocyclic couplers, and the acid addition salts thereof.

50. The composition according claim 38, wherein the couplers are present in an amount ranging from 0.0001 to 10% by weight, relative to the total weight of the composition.

51. The composition according to claim 38, wherein the at least one oxidation dye comprises an acid addition salt of the oxidation dye, and wherein the acid addition salt is chosen from hydrochlorides, hydrobromides, sulphates, tartrates, lactates and acetates.

52. The composition according to claim 1, wherein the direct dyes are chosen from neutral, acidic and cationic nitro benzene direct dyes, neutral, acidic and cationic azo direct dyes, neutral, acidic and cationic quinone and anthraquinone direct dyes, azine direct dyes, triarylmethane direct dyes, indoamine direct dyes, and natural direct dyes.

53. The composition according to claim 1, wherein the at least one dye is present in an amount ranging from 0.001 to 20% by weight, relative to the total weight of the composition.

54. The composition according to claim 53, wherein the at least one dye is present in an amount ranging from 0.005 to 10% by weight, relative to the total weight of the composition.

55. The composition according to claim 1 further comprising at least one reducing agent an amount ranging from 0.05 to 3% by weight, relative to the total weight of the composition.

56. The composition according to claim 1, further comprising at least one oxidizing agent.

57. The composition according to claim 56, wherein the at least one oxidizing agent is chosen from hydrogen peroxide, urea peroxide, alkali metal bromates and ferricyanides, persalts, and redox enzymes present where appropriate with their respective donor or cofactor.

58. The composition according to claim 57, wherein the at least one oxidizing agent comprises hydrogen peroxide.

59. The composition according to claim 58, wherein the at least one oxidizing agent comprises a hydrogen peroxide solution having a titre ranging from 1 to 40 volumes.

60. The composition according to claim 1, wherein said composition has a pH ranging from 4 to 11.

61. A process for dyeing keratin fibres, comprising applying to the fibres a colouring composition comprising, in a cosmetically acceptable medium, at least one direct dye and at least one aminosilicone chosen from formulae (I) and (II):

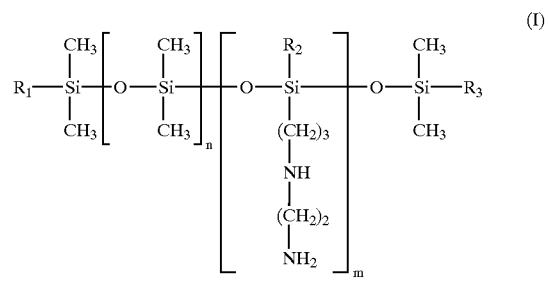

wherein:
m and n are numbers with a sum (n+m) ranging from 1 to 1000;
n is a number ranging from 0 to 999 and m is a number ranging from 1 to 1000;
$R_1$, $R_2$ and $R_3$, which may be identical or different, are chosen from a hydroxyl radical and $C_1$–$C_4$ alkoxy radicals, at least one of the radicals $R_1$ to $R_3$ being an alkoxy radical;

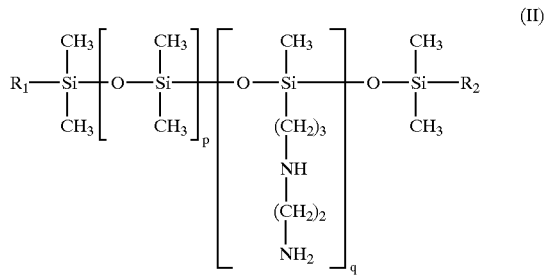

wherein:
p and q are numbers with a sum (p+q) ranging from 1 to 1000;
p is a number ranging from 0 to 999, and q is a number ranging from 1 to 1000;
$R_1$ and $R_2$, which are different, are chosen from hydroxyl radicals and $C_1$–$C_4$ alkoxy radicals, at least one of the radicals $R_1$ and $R_2$ being an alkoxy radical.

62. The process according to claim 61, wherein the keratin fibres are hair.

63. A process for dyeing keratin fibres, comprising:
(a) applying to the fibres at least one colouring composition comprising, in a cosmetically acceptable medium, at least one dye chosen from direct dyes and oxidation dyes, and at least one aminosilicone chosen from formulae (I) and (II):

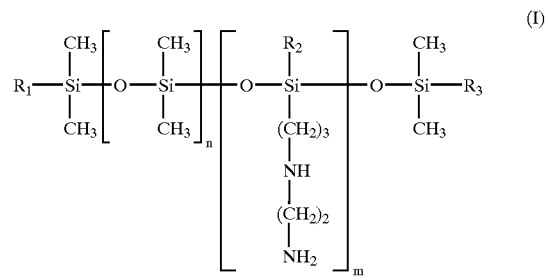

wherein:
m and n are numbers with a sum (n+m) ranging from 1 to 1000;

n is a number ranging from 0 to 999 and m is a number ranging from 1 to 1000;

$R_1$, $R_2$ and $R_3$, which may be identical or different, are chosen from a hydroxyl radical and $C_1$–$C_4$ alkoxy radicals, at least one of the radicals $R_1$ to $R_3$ being an alkoxy radical;

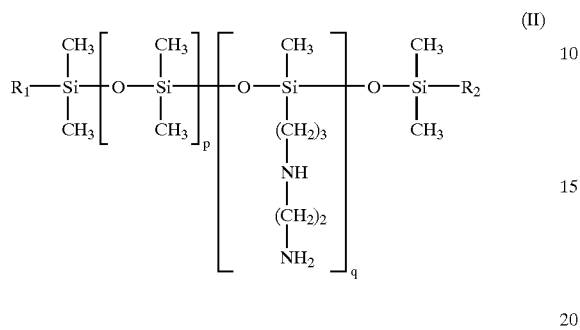

(II)

wherein:

p and q are numbers with a sum (p+q) ranging from 1 to 1000;

p is a number ranging from 0 to 999, and q is a number ranging from 1 to 1000;

$R_1$ and $R_2$, which are different, are chosen from hydroxyl radicals and $C_1$–$C_4$ alkoxy radicals, at least one of the radicals $R_1$ and $R_2$ being an alkoxy radical; and (b) applying to the fibres at least one oxidizing composition comprising at least one oxidizing agent.

64. The process according to claim 63, wherein the keratin fibres are hair.

65. The process according to claim 63, wherein the at least one oxidizing composition is combined, at the time of use, with the at least one colouring composition.

66. The process according to claim 63, wherein the at least one oxidizing composition is applied sequentially with the at least one colouring composition without rinsing in between.

67. The process according to claim 63 wherein the colour of the fibres is developed at an alkaline, neutral or acidic pH.

68. A process for dyeing keratin fibres, comprising:

(a) applying to wet or dry keratin fibres a colouring composition or ready to use composition, produced extemporaneously at the time of use from coloring and oxidizing compositions; wherein the colouring composition comprises, in a cosmetically acceotable medium, at least one dye chosen from direct dyes and oxidation dyes, and further comptising at keast one aminosilicone chosen from formula (I) and (II)

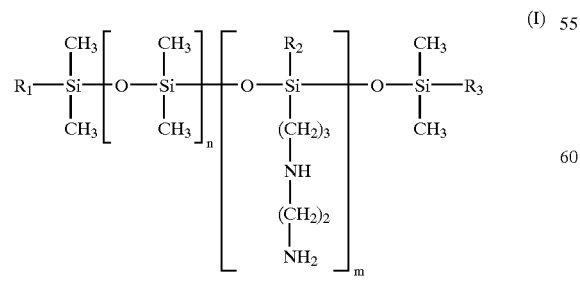

(I)

wherein m and n are numbers with a sum (n+m) ranging from 1 to 1000, n is a number ranging from 0 to 999, and m is a number ranging from 1 to 1000, $R_1$, $R_2$ and $R_3$, which may be identical or different, are chosen from a hydroxyl radical and $C_1$–$C_4$ alkoxy radicals, at least one of the radicals $R_1$ to $r_3$ being an alkoxy radical;

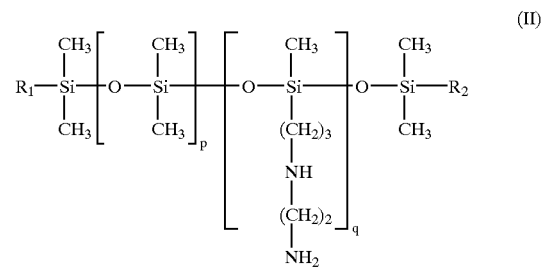

(II)

wherein:

p and q are numbers with a sum (p+q) ranging from 'to 1000, p is a mumber ranging from 0 to 999, and q is a number ranging from 1 to 1000, $R_1$ and $R_2$, which are different, are chosen from hydroxyl radicals and $C_1$–$C_4$ alkoxy radicals, at least one of the radicals $R_1$ and $R_2$ being an alkoxy radical (b) leaving the colouring composition or ready to use composition in contact with the human keratin fibres for a period of time ranging from 1 to 60 minutes; and (c) rinsing the fibres.

69. The process according to claim 68, wherein the period of time ranges from 10 to 45 minutes.

70. The process according to claim 68, further comprising washing the fibres with shampoo, rinsing the fibres, and drying the fibres.

71. A multi-compartment device or kit for dyeing keratin fibres, comprising multiple compartments, wherein a first compartment comprises a composition comprising, in a cosmetically acceptable medium, at least one dye chosen from direct dyes and oxidation dyes, and at least one aminosilicone chosen from formulae (I) and (II):

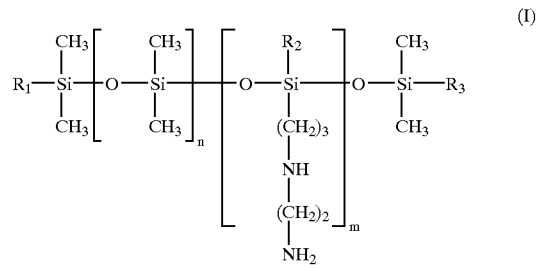

(I)

wherein:

m and n are numbers with a sum (n+m) ranging from 1 to 1000;

n is a number ranging from 0 to 999 and m is a number ranging from 1 to 1000;

$R_1$, $R_2$ and $R_3$, which may be identical or different, are chosen from a hydroxyl radical and $C_1$–$C_4$ alkoxy radicals, at least one of the radicals $R_1$ to $R_3$ being an alkoxy radical;

(II)

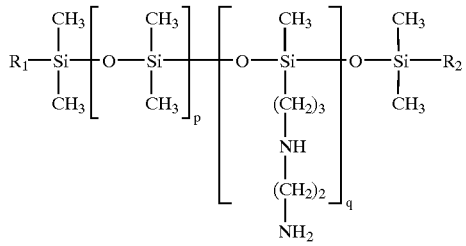

wherein:

p and q are numbers with a sum (p+q) ranging from 1 to 1000;

p is a number ranging from 0 to 999, and q is a number ranging from 1 to 1000;

$R_1$ and $R_2$, which are different, are chosen from hydroxyl radicals and $C_1$–$C_4$ alkoxy radicals, at least one of the radicals $R_1$ and $R_2$ being an alkoxy radical; and wherein a second compartment comprises a composition comprising, in a cosmetically acceptable medium, at least one oxidizing agent.

72. The multi-compartment device or kit according to claim 71, wherein the keratin fibres are hair.

73. A multi-compartment device or kit for dyeing keratin fibres comprising multiple compartments, wherein a first compartment comprises a composition comprising, in a cosmetically acceptable medium, at least one dye chosen from direct dyes and oxidation dyes, wherein a second compartment comprises a composition comprising, in a cosmetically acceptable medium, at least one oxidizing agent; and wherein a third compartment comprises a composition comprising, in a cosmetically acceptable medium, at least one aminosilicone chosen from formulae (I) and (II):

(I)

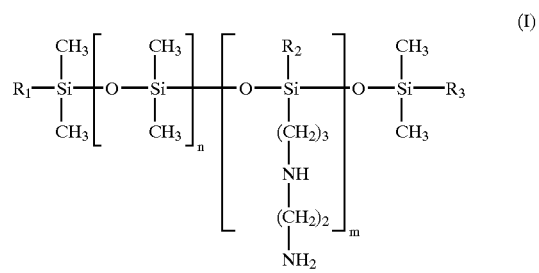

wherein:

m and n are numbers with a sum (n+m) ranging from 1 to 1000;

n is a number ranging from 0 to 999 and m is a number ranging from 1 to 1000;

$R_1$, $R_2$ and $R_3$, which may be identical or different, are chosen from a hydroxyl radical and $C_1$–$C_4$ alkoxy radicals, at least one of the radicals $R_1$ to $R_3$ being an alkoxy radical;

(II)

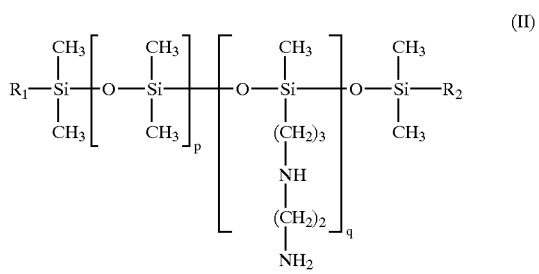

wherein:

p and q are numbers with a sum (p+q) ranging from 1 to 1000, p is a number ranging from 0 to 999, and q is a number ranging from 1 to 1000;

$R_1$ and $R_2$, which are different, are chosen from hydroxyl radicals and $C_1$–$C_4$ alkoxy radicals, at least one of the radicals $R_1$ and $R_2$ being an alkoxy radical.

74. The multi-compartment kit according to claim 73, wherein the keratin fibres are human hair.

* * * * *

UNITED STATES PATENT AND TRADEMARK OFFICE
CERTIFICATE OF CORRECTION

PATENT NO. : 6,846,333 B2
DATED : January 25, 2005
INVENTOR(S) : Frédéric Legrand et al.

It is certified that error appears in the above-identified patent and that said Letters Patent is hereby corrected as shown below:

Column 31,
Line 22, "according claim 38," should read -- according to claim 38, --.
Line 47, "agent an amount" should read -- agent in an amount --.

Column 33,
Line 48, "coloring" should read -- colouring --.
Line 49, "compositions;" should read -- compositions, --.
Line 50, "acceotable" should read -- acceptable --.
Line 52, "comptising at keast" should read -- comprising at least --.

Column 34,
Lines 4 and 28, "1000," should read -- 1000; --.
Line 8, "r$_3$" should read -- R$_3$ --.
Line 25, "to" should read -- 1 to --.
Line 27, "mumber" should read -- number --.

Signed and Sealed this

Tenth Day of May, 2005

JON W. DUDAS
*Director of the United States Patent and Trademark Office*